(12) United States Patent
Goto et al.

(10) Patent No.: US 10,751,462 B2
(45) Date of Patent: Aug. 25, 2020

(54) MEDICAL APPARATUS

(71) Applicant: Nikkiso Company Limited, Tokyo (JP)

(72) Inventors: Hitoshi Goto, Shizuoka (JP); Masahiro Toyoda, Shizuoka (JP); Tomoya Murakami, Shizuoka (JP); Shigeaki Funamura, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 183 days.

(21) Appl. No.: 15/686,289

(22) Filed: Aug. 25, 2017

(65) Prior Publication Data

US 2017/0348471 A1 Dec. 7, 2017

Related U.S. Application Data

(63) Continuation of application No. PCT/JP2016/055939, filed on Feb. 26, 2016.

(30) Foreign Application Priority Data

Feb. 27, 2015 (JP) .................................. 2015-038070

(51) Int. Cl.
*A61M 1/36* (2006.01)
*A61M 1/16* (2006.01)
(Continued)

(52) U.S. Cl.
CPC ......... *A61M 1/3656* (2014.02); *A61B 5/0402* (2013.01); *A61B 5/0408* (2013.01);
(Continued)

(58) Field of Classification Search
CPC ........ A61M 1/30; A61M 1/3656; A61M 1/16; A61M 1/36; A61M 1/3653; A61M 5/0402;
(Continued)

(56) References Cited

U.S. PATENT DOCUMENTS 9,308,332 B2  4/2016 Heppe
2005/0038325 A1* 2/2005 Moll .................. A61B 5/02042
                                                              600/300
2013/0096481 A1* 4/2013 Roger ................ A61M 1/3653
                                                              604/6.09

FOREIGN PATENT DOCUMENTS

JP 2013-530753 A1 8/2013
JP 2014-083071    5/2014
(Continued)

OTHER PUBLICATIONS

International Search Report from the Japanese Patent Office for Application No. PCT/JP2016/055939 dated May 6, 2016.

*Primary Examiner* — Philip R Wiest
(74) *Attorney, Agent, or Firm* — Young Basile Hanlon & MacFarlane, P.C.

(57) ABSTRACT

A medical apparatus in which the measurement of an electrocardiogram and the detection of blood leakage that may occur if an accessing unit comes off the patient can be performed accurately without fail, and with which the efficiency in the operation to be performed before the treatment can be improved. A medical apparatus includes a blood purification device including an accessing unit formed of a venous puncture needle stickable into a patient, electrocardiogram-measuring devices closely attached to a skin of the patient and being capable of measuring an electrocardiogram of the patient, and a blood-leakage-detecting device attached to a position near the accessing unit and being capable of detecting blood of the patient that may leak from the accessing unit. The medical apparatus further includes an integrated detecting device provided as a unit including the electrocardiogram-measuring device and the blood-leakage-detecting device.

20 Claims, 6 Drawing Sheets

(51) Int. Cl.
*A61B 5/0402* (2006.01)
*A61B 5/0408* (2006.01)
*A61M 1/30* (2006.01)
*A61M 5/50* (2006.01)

(52) U.S. Cl.
CPC ............... *A61M 1/16* (2013.01); *A61M 1/30* (2013.01); *A61M 1/36* (2013.01); *A61M 1/3653* (2013.01); *A61M 5/5086* (2013.01); *A61M 2205/15* (2013.01); *A61M 2230/04* (2013.01)

(58) Field of Classification Search
CPC .............. A61M 5/0408; A61M 5/5086; A61M 2205/15; A61M 2230/04
See application file for complete search history.

(56) References Cited

FOREIGN PATENT DOCUMENTS

| | | |
|---|---|---|
| WO | 2005/019416 A2 | 3/2005 |
| WO | 2008/100670 A1 | 8/2008 |
| WO | 2011/160807 A1 | 12/2011 |

* cited by examiner

[Fig 1]

[Fig 2]
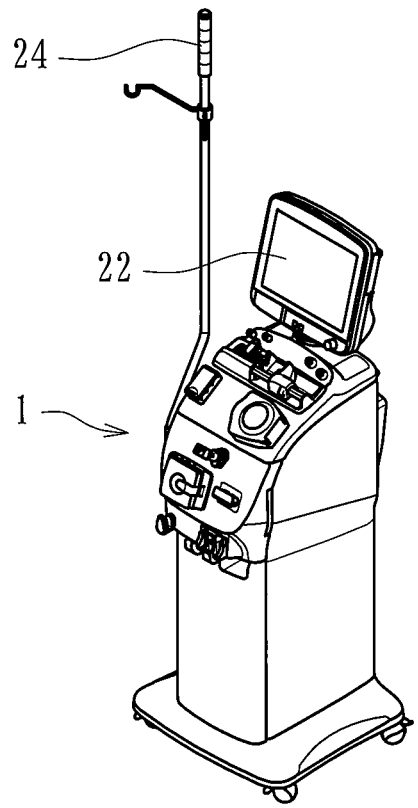
[Fig 3]
(a)
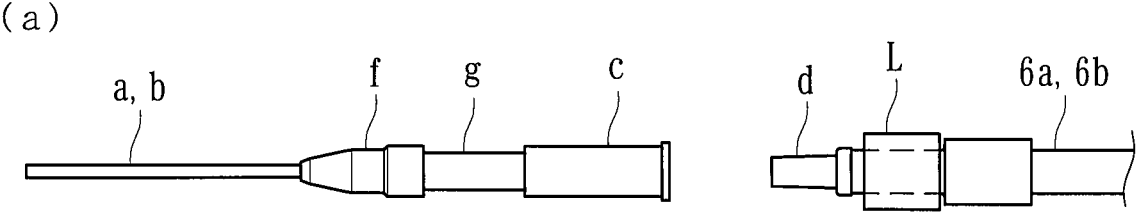
(b)
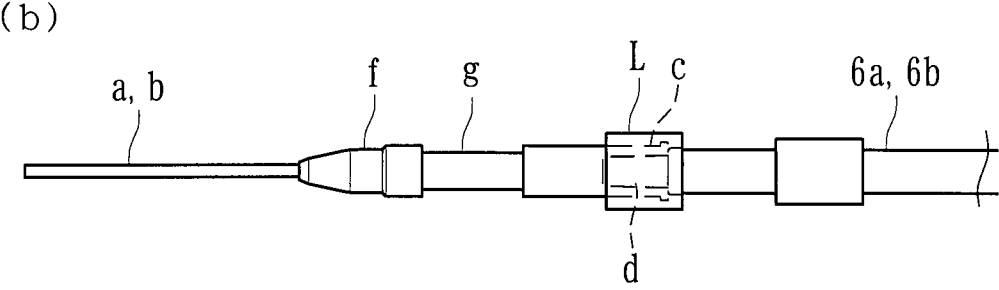

[Fig 4]
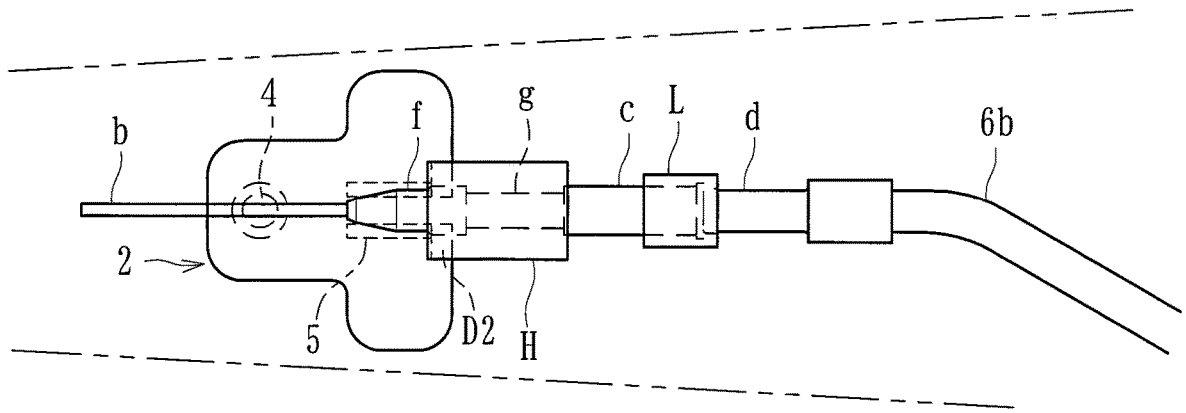
[Fig 5]
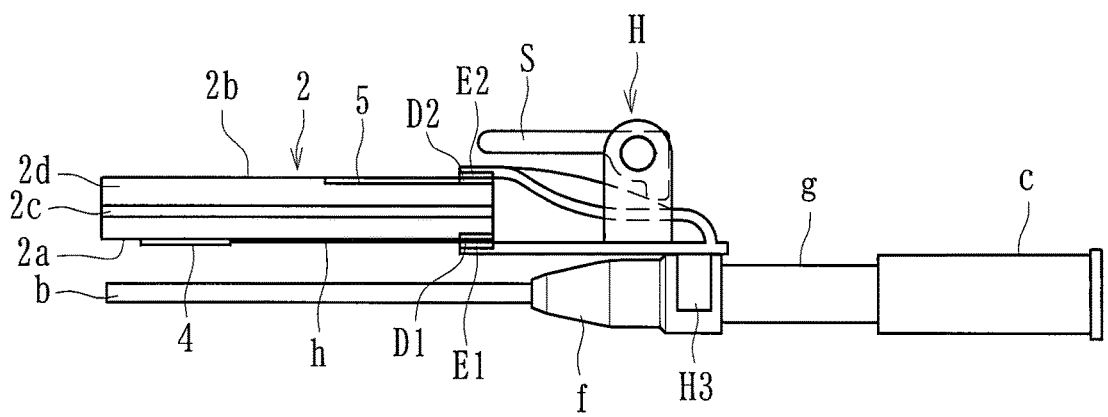
[Fig 6]
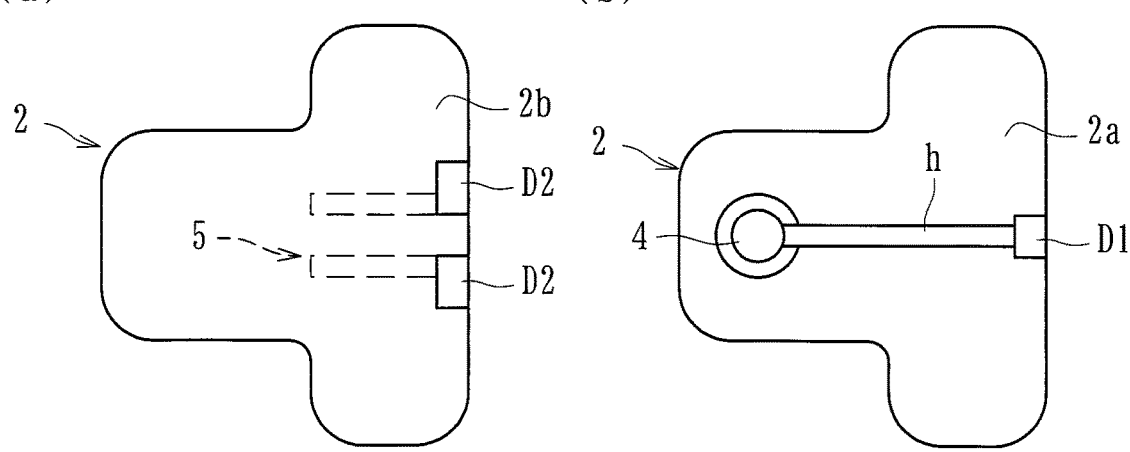

[ Fig 7 ]
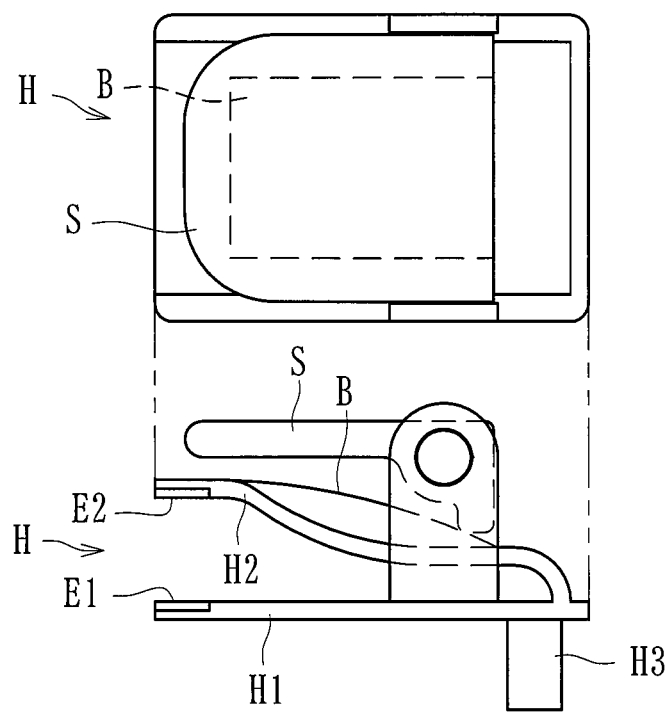
[ Fig 8 ]
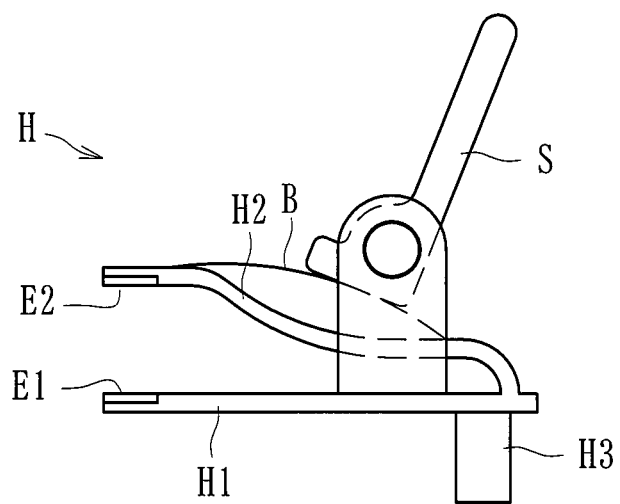

[ Fig 9 ]
[ Fig 10 ]
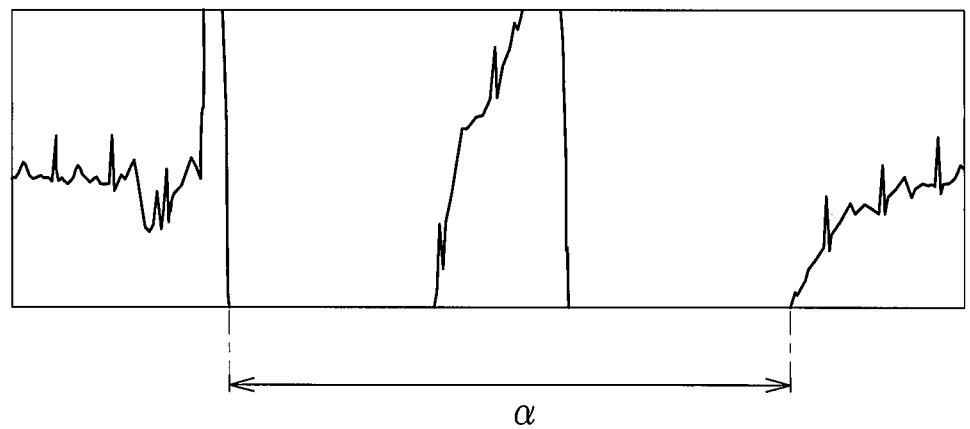
[ Fig 11 ]
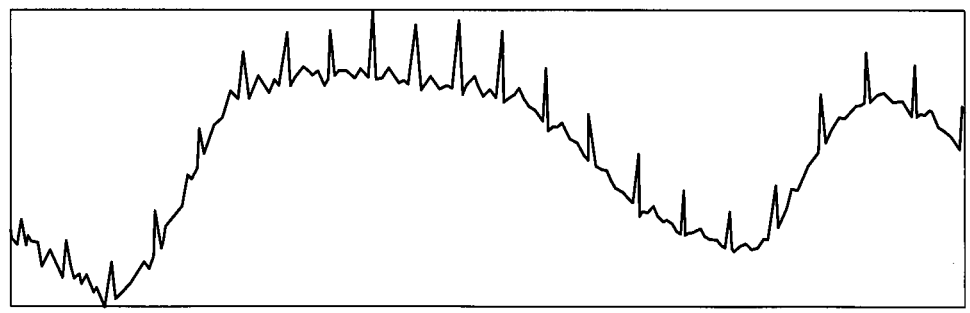

[Fig 12]
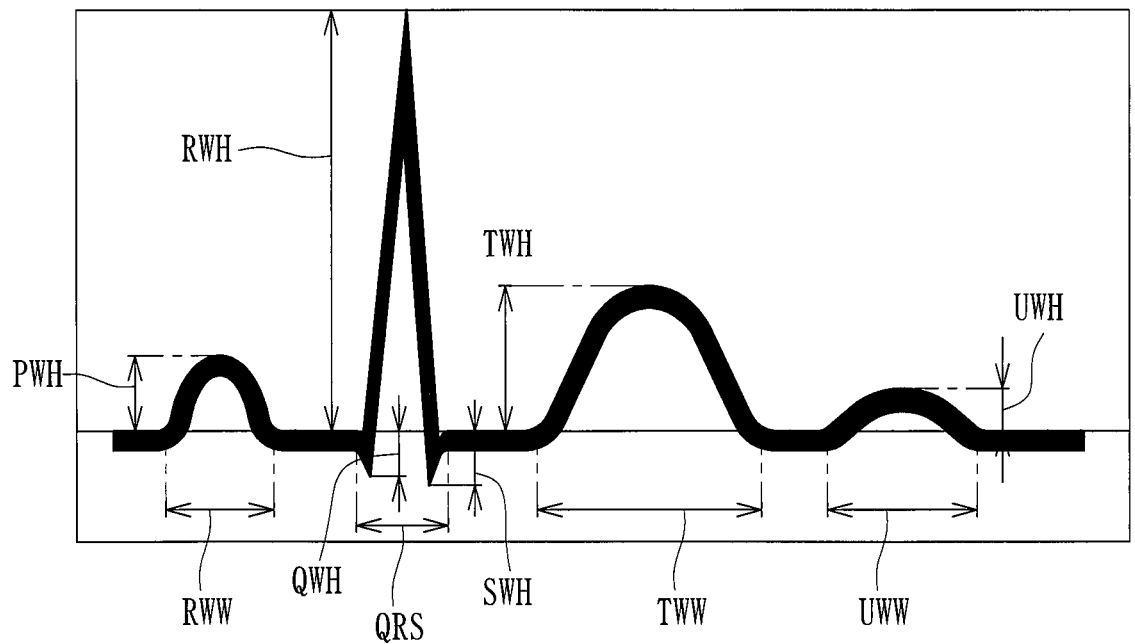
PWH: P-wave height
RWH: R-wave height
TWH: T-wave height
UWH: U-wave height
RWW: R-wave width
QWH: Q-wave height
QRS: QRS-Complex width
SWH: S-wave height
TWW: T-wave width
UWW: U-wave width

MEDICAL APPARATUS

FIELD

The present teachings relate to a medical apparatus including an electrocardiogram-measuring device capable of measuring the electrocardiogram of a patient, and a blood-leakage-detecting device attached to a position near an accessing unit and being capable of detecting blood of the patient that may leak from the accessing unit.

BACKGROUND

In general, dialysis treatment is performed by using a dialysis treatment apparatus including a blood circuit for extracorporeally circulating the blood of a patient, a dialyzer connected to a halfway point of the blood circuit, a peristaltic blood pump, and a dialysis-apparatus body capable of performing ultrafiltration while performing hemodialysis treatment in which dialysate is introduced into or delivered from the dialyzer. Typically, dialysis treatment performed with such a dialysis treatment apparatus continues for about four hours and is given every other day. Therefore, the hemodynamics of the patient during the treatment changes significantly. In particular, it is important to efficiently and assuredly prevent the decrease in blood pressure caused by the removal of excessive water (ultrafiltration).

Furthermore, many of patients who need to take dialysis treatment also suffer from cardiovascular complications such as arrhythmia. Therefore, abnormality in circulatory dynamics and the cause thereof need to be grasped by monitoring the heartbeat, the pulse, and so forth. One of general measures for monitoring such information on the heartbeat and the pulse of the patient is the use of an electrocardiograph capable of measuring an electrocardiogram. For example, during blood purification treatment, at least a pair of electrodes (electrocardiogram-measuring devices) are closely attached to the patient, and the electrocardiogram of the patient is measured on the basis of the potentials of the electrodes.

On the other hand, in blood purification treatment, an arterial puncture needle and a venous puncture needle are stuck into the patient, and the blood of the patient is collected through the arterial puncture needle and is extracorporeally circulated through a blood circuit so that the blood is purified. Then, the blood thus purified needs to be returned to the patient through the venous puncture needle. Hence, in the process of extracorporeal blood circulation, the puncture needles may each accidentally come off the site of the patient where the needle is stuck when, for example, the patient makes any move. In particular, if the venous puncture needle comes off, some blood may leak to the outside. To detect such coming off of the puncture needle, the known art employs detection of blood leakage from the puncture needle by using a blood leakage sensor or the like (see PTL 1, for example).

PATENT LITERATURE

PTL 1: Japanese Unexamined Patent Application Publication (Translation of PCT Application) No. 2013-530753

SUMMARY

However, since the above known art requires the pair of electrodes (the electrocardiogram-measuring devices) for measuring the electrocardiogram and the sensor (the blood-leakage-detecting device) for detecting blood leakage, the known art has a problem in that the necessity of attaching those electrodes and the sensor before the treatment lowers the efficiency in the operation to be performed before the treatment. Furthermore, to detect blood leakage that may occur during the treatment, such blood leaking from the puncture needle needs to touch the blood leakage sensor. However, the blood does not necessarily leak at the position where the blood leakage sensor is provided. Therefore, it is difficult to detect blood leakage accurately without fail. The above problem is not limited to the case of blood purification treatment and also applies to, for example, a case of infusion treatment in which a catheter is inserted into a blood vessel of the patient and a drug or the like is infused into the body of the patient (in such a case, however, the object that may leak is an infusion solution).

The present teachings have been conceived in view of the above circumstances and provides a medical apparatus in which the measurement of the electrocardiogram and the detection of blood leakage that may occur if an accessing unit comes off the patient can be performed accurately without fail, and with which the efficiency in the operation to be performed before and during the treatment (including the blood-returning process in the case of blood purification treatment) can be improved.

According to the teachings herein, there is provided a medical apparatus that includes a treatment device including an accessing unit formed of either a puncture needle stickable into a patient or a catheter insertable into a blood vessel of the patient, an electrocardiogram-measuring device closely attached to a skin of the patient and being capable of measuring an electrocardiogram of the patient, and a blood-leakage-detecting device attached to a position near the accessing unit and being capable of detecting blood of the patient that may leak from the accessing unit. The medical apparatus further includes an integrated detecting device provided as a unit including the electrocardiogram-measuring device and the blood-leakage-detecting device.

According to the teachings herein, in the medical apparatus according to the present teachings, the integrated detecting device has a close-contact surface that is brought into close contact with the skin of the patient and a non-close-contact surface that is out of close contact with the skin of the patient, the close-contact surface being provided with the electrocardiogram-measuring device, the non-close-contact surface being provided with the blood-leakage-detecting device.

According to the teachings herein, in the medical apparatus according to the present teachings, the close-contact surface and the non-close-contact surface are a front surface and a back surface, respectively, of the integrated detecting device, one side of which corresponds to the close-contact surface and is provided with the electrocardiogram-measuring device, and an other side of which corresponds to the non-close-contact surface and is provided with the blood-leakage-detecting device.

According to the teachings herein, in the medical apparatus according to the present teachings, the integrated detecting device is a flexible sheet-like member with an insulating layer interposed between the close-contact surface on the one side and the non-close-contact surface on the other side.

According to the teachings herein, in the medical apparatus according to the present teachings, the close-contact surface adheres to the skin of the patient and allows the electrocardiogram-measuring device to be in close contact with the patient, and the non-close-contact surface is provided with a moisture-absorbing member, the moisture-absorbing member absorbing blood that may leak from the accessing unit and allowing the blood-leakage-detecting device to detect blood leakage.

According to the teachings herein, the medical apparatus according to the teachings herein further includes an electrocardiogram-acquiring device that acquires the electrocardiogram on the basis of a measurement signal transmitted from the electrocardiogram-measuring device, and a blood-leakage-monitoring device that monitors whether or not there is any blood leakage on the basis of a detection signal transmitted from the blood-leakage-detecting device. Coming off of the accessing unit from the patient is detectable on the basis of electrocardiographic information acquired by the electrocardiogram-acquiring device and blood-leakage information acquired by the blood-leakage-monitoring device.

According to the teachings herein, the medical apparatus includes the integrated detecting device provided as a unit including the electrocardiogram-measuring device and the blood-leakage-detecting device, the electrocardiogram-measuring device being closely attached to the skin of the patient and being capable of measuring the electrocardiogram of the patient, the blood-leakage-detecting device being attached to the position near the accessing unit and being capable of detecting the blood of the patient that may leak from the accessing unit. Hence, the measurement of the electrocardiogram and the detection of blood leakage occurring if the accessing unit comes off the patient can be performed accurately without fail. Furthermore, the efficiency in the operation to be performed before the treatment can be improved.

According to the teachings herein, the integrated detecting device has the close-contact surface that is brought into close contact with the skin of the patient and the non-close-contact surface that is out of close contact with the skin of the patient. Furthermore, the close-contact surface is provided with the electrocardiogram-measuring device, and the non-close-contact surface is provided with the blood-leakage-detecting device. Hence, blood leakage that may occur if the accessing unit comes off the patient can be detected assuredly while the electrocardiogram of the patient is measured accurately.

According to the teachings herein, the close-contact surface and the non-close-contact surface are the front surface and the back surface, respectively, of the integrated detecting device, one side of which corresponds to the close-contact surface and is provided with the electrocardiogram-measuring device, and the other side of which corresponds to the non-close-contact surface and is provided with the blood-leakage-detecting device. Hence, blood leakage that may occur if the accessing unit comes off the patient can be detected more assuredly while the electrocardiogram of the patient is measured more accurately.

According to the teachings herein, the integrated detecting device is the flexible sheet-like member with the insulating layer interposed between the close-contact surface on the one side and the non-close-contact surface on the other side. Hence, the electrocardiogram-measuring device provided on the flexible sheet-like member can be brought into close contact with the skin of the patient in a good manner, and the presence of the insulating layer can prevent the occurrence of errors that may be caused by the interference between a measurement signal from the electrocardiogram-measuring device and a detection signal from the blood-leakage-detecting device.

According to the teachings herein, the close-contact surface adheres to the skin of the patient and allows the electrocardiogram-measuring device to be in close contact with the patient, and the non-close-contact surface is provided with the moisture-absorbing member, the moisture-absorbing member absorbing blood that may leak from the accessing unit and allowing the blood-leakage-detecting device to detect blood leakage. Hence, the detection of blood leakage by the blood-leakage-detecting device can be performed more assuredly while the measurement of the electrocardiogram by the electrocardiogram-measuring device is performed more accurately.

According to the teachings herein, the medical apparatus further includes the electrocardiogram-acquiring device that acquires the electrocardiogram on the basis of the measurement signal transmitted from the electrocardiogram-measuring device, and the blood-leakage-monitoring device that monitors whether or not there is any blood leakage on the basis of the detection signal transmitted from the blood-leakage-detecting device. Furthermore, coming off of the accessing unit from the patient is detectable on the basis of the electrocardiographic information acquired by the electrocardiogram-acquiring device and the blood-leakage information acquired by the blood-leakage-monitoring device. Hence, the occurrence of any blood leakage from the accessing unit can be detected not only by the blood-leakage-monitoring device but also by the electrocardiogram-acquiring device.

BRIEF DESCRIPTION

FIG. 1 is an overall schematic diagram of a medical apparatus according to an embodiment of the present invention.

FIG. 2 is a perspective view of a treatment device included in the medical apparatus.

FIG. 3 illustrates a puncture needle attached to the distal end of a blood circuit included in the medical apparatus, including part (a) illustrating a state where the puncture needle is yet to be attached, and part (b) illustrating a state where the puncture needle has been attached.

FIG. 4 is a schematic diagram illustrating a state where an integrated detecting device included in the medical apparatus has been attached to a patient.

FIG. 5 is a schematic side view of the integrated detecting device included in the medical apparatus.

FIG. 6 includes schematic diagrams illustrating the front side (a) and the back side (b), respectively, of the integrated detecting device included in the medical apparatus.

FIG. 7 includes a plan view and a side view of a holding unit (in a locked state) that holds the integrated detecting device included in the medical apparatus.

FIG. 8 is a side view of the holding unit (yet to be locked).

FIG. 9 is a graph of an electrocardiogram (in a normal state) measured by electrocardiogram-measuring devices included in the medical apparatus.

FIG. 10 is a graph of an electrocardiogram (at the occurrence of coming off) measured by the electrocardiogram-measuring devices included in the medical apparatus.

FIG. 11 is a graph of an electrocardiogram (with the baseline fluctuating with perspiration) measured by the electrocardiogram-measuring devices included in the medical apparatus.

FIG. 12 is a graph illustrating the waveform of the electrocardiogram measured by the electrocardiogram-measuring devices included in the medical apparatus.

DETAILED DESCRIPTION

An embodiment of the present invention will now be described specifically with reference to the drawings.

Figure 1:
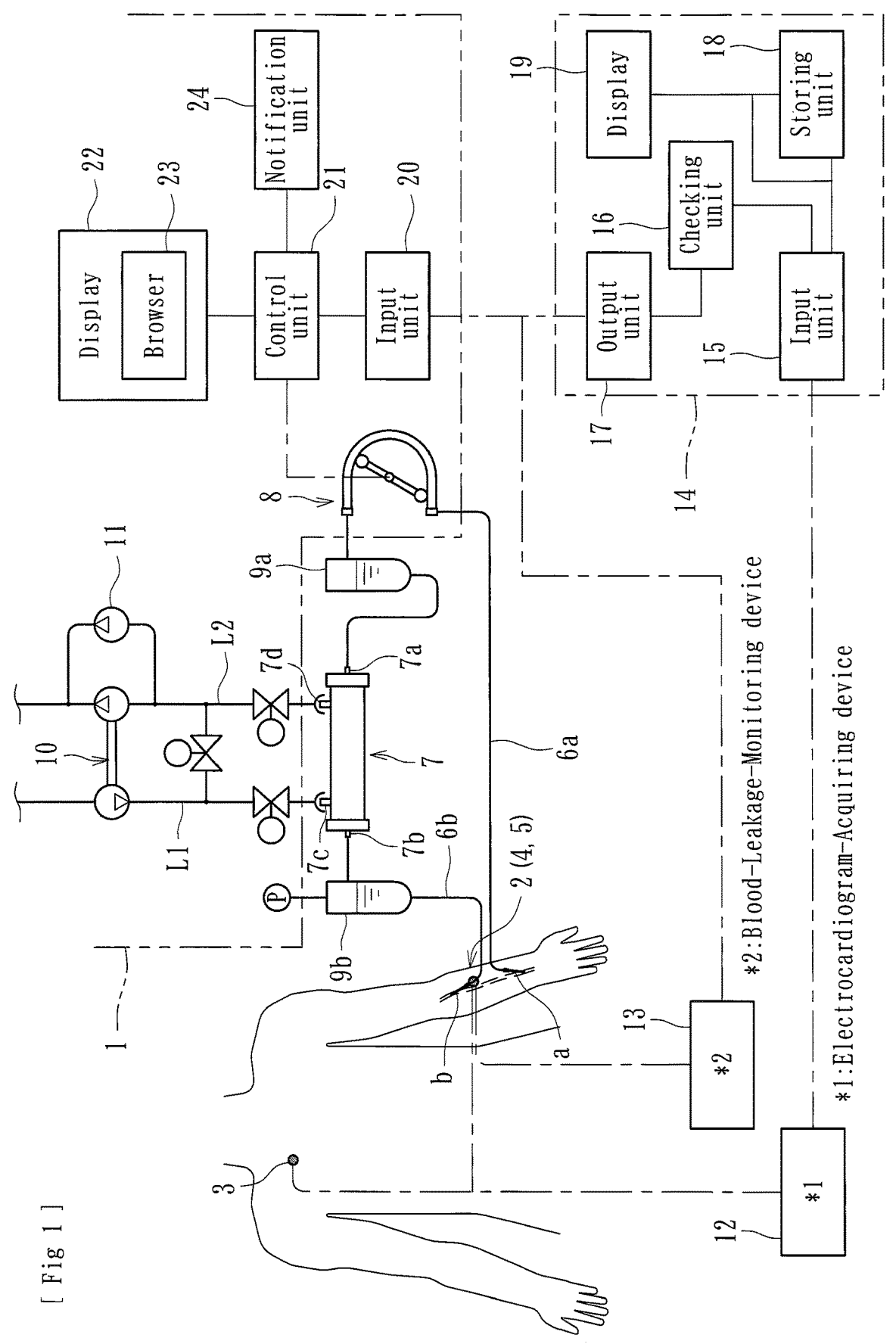

As illustrated in FIG. 1, a medical apparatus according to the embodiment includes a blood purification device 1 as a treatment device, an integrated detecting device 2, electrocardiogram-measuring devices 3 and 4, a blood-leakage-detecting device 5 (see FIGS. 1, 5, and 6), an electrocardiogram-acquiring device 12, a blood-leakage-monitoring device 13, and an external information-processing device 14. The blood purification device 1 is electrically connected to the external information-processing device 14 and to the blood-leakage-monitoring device 13, and the external information-processing device 14 is electrically connected to the electrocardiogram-acquiring device 12, so that signals can be transmitted to and received from one another. The blood purification device 1 includes blood circuits (6a and 6b), a dialyzer 7, and puncture needles (an arterial puncture needle (a) and a venous puncture needle (b). The puncture needles serve as accessing units.

The blood purification device 1 according to the present embodiment is a hemodialysis device for performing hemodialysis treatment and ultrafiltration while extracorporeally circulating the blood of a patient and includes, as illustrated in FIGS. 1 and 2, the blood circuits (6a and 6b) for extracorporeally circulating the blood of the patient, the dialyzer 7 as a blood purifier connected to the blood circuits (6a and 6b) and provided for performing hemodialysis treatment, a dialysate introduction line L1 connected to the dialyzer 7 and through which dialysate is supplied to the dialyzer 7, and a dialysate drain line L2 connected to the dialyzer 7 and through which drain liquid is discharged from the dialyzer 7.

The blood circuits are formed of flexible tubes that allow liquid such as blood to flow therethrough and include an arterial blood circuit 6a and a venous blood circuit 6b. The arterial puncture needle a (see FIGS. 1 and 3) is connectable to the distal end of the arterial blood circuit 6a. Furthermore, a peristaltic blood pump 8 and an air-trap chamber 9a for bubble removal are provided at respective halfway positions of the arterial blood circuit 6a. On the other hand, the venous puncture needle b (see FIGS. 1 and 3) is connected to the distal end of the venous blood circuit 6b. Furthermore, an air-trap chamber 9b for bubble removal is provided at a halfway position of the venous blood circuit 6b.

The arterial puncture needle a and the venous puncture needle b according to the present embodiment each correspond to "the accessing unit" (a puncture needle stickable into the patient) according to the present invention and are each a cannula (to be placed in a blood vessel) (a catheter) attached to, as illustrated in FIG. 3, a distal part f made of rigid resin or the like. The distal part f is connected to a joint c, made of rigid resin or the like, with a forceps-held flexible tube g interposed therebetween. As illustrated in FIG. 3(a), the distal part f, the forceps-held flexible tube g, and the joint c are integrated into a single unit.

On the other hand, the arterial blood circuit 6a and the venous blood circuit 6b are each provided at the distal end thereof with a joint (d) made of rigid resin or the like. As illustrated in FIG. 3(b), the joint c connected to the puncture needle is fitted onto the joint (d) and is screwed thereon with a lock ring (L) so as to be locked while being fitted thereon. If the forceps-held flexible tube (g) is pinched by a pair of forceps, the flow route between the arterial puncture needle (a) or the venous puncture needle (b) and the arterial blood circuit 6a or the venous blood circuit 6b can be intercepted.

When the peristaltic blood pump 8 is activated with the arterial puncture needle (a) and the venous puncture needle (b) stuck in the patient, the blood of the patient collected from the arterial puncture needle a flows through the arterial blood circuit 6a to the dialyzer 7, where the blood is purified. Then, the blood undergoes bubble removal in the air-trap chamber 9b, flows through the venous blood circuit 6b, and returns into the body of the patient through the venous puncture needle (b). Thus, the blood of the patient can be purified by the dialyzer 7 while being extracorporeally circulated through the blood circuits (6a and 6b).

The dialyzer 7 has, in a housing thereof, a blood introduction port 7a, a blood delivery port 7b, a dialysate introduction port 7c, and a dialysate delivery port 7d. Among these, the blood introduction port 7a receives the proximal end of the arterial blood circuit 6a, and the blood delivery port 7b receives the proximal end of the venous blood circuit 6b. The dialysate introduction port 7c and the dialysate delivery port 7d are connected to the dialysate introduction line L1 and the dialysate drain line L2, respectively, extending from the blood purification device 1.

The housing of the dialyzer 7 houses a plurality of hollow fibers. The hollow fibers provide blood channels thereinside, and spaces between the inner peripheral surface of the housing and the outer peripheral surfaces of the hollow fibers serve as dialysate channels. The hollow fibers each have a number of very small holes (pores) extending therethrough from the outer peripheral surface to the inner peripheral surface, thereby forming a hollow fiber membrane. Hence, impurities and the like contained in the blood are allowed to penetrate through the membrane into the dialysate.

As illustrated in FIG. 1, the blood purification device 1 includes a duplex pump 10 provided over the dialysate introduction line L1 and the dialysate drain line L2, and an ultrafiltration pump 11 connected to a bypass line that bypasses the duplex pump 10 in the dialysate drain line L2. One end of the dialysate introduction line L1 is connected to the dialyzer 7 (the dialysate introduction port 7c), and the other end is connected to a dialysate-supplying device (not illustrated) that prepares a dialysate having a predetermined concentration. One end of the dialysate drain line L2 is connected to the dialyzer 7 (the dialysate delivery port 7d), and the other end is connected to a drainage device (not illustrated). Hence, the dialysate supplied from the dialysate-supplying device flows through the dialysate introduction line L1, reaches the dialyzer 7, and is delivered to the drainage device through the dialysate drain line L2.

The ultrafiltration pump 11 is provided for removing water from the blood of the patient that flows through the dialyzer 7. Specifically, when the ultrafiltration pump 11 is activated, the amount of liquid discharged from the dialysate drain line L2 becomes larger than the amount of dialysate introduced from the dialysate introduction line L1, and water is removed from the blood by an amount corresponding to the surplus. The removal of water from the blood of the patient may be performed by using another device (for example, a device employing a so-called balancing chamber or the like) instead of using the duplex pump 10 and the ultrafiltration pump 11.

The blood purification device 1 according to the present embodiment includes an input unit 20, a control unit 21, a display 22, and a notification unit 24. For example, the display 22 is capable of displaying information on the blood purification treatment in real time. As illustrated in FIG. 2, the display 22 includes, for example, a touch-panel liquid-crystal screen on which various pieces of information are displayable. What is to be displayed is controlled by the control unit 21. The control unit 21, which controls the items to be displayed on the display 22, is electrically connected to actuators provided for the blood pump 8 and other devices and is also capable of controlling those actuators.

The input unit 20 is connected to the control unit 21 and is electrically connected to an output unit 17 included in the external information-processing device 14. Information (data) outputted from the output unit 17 is inputtable into the input unit 20. Hence, information inputted into the input unit 20 can be transmitted to the control unit 21 and be displayed on the display 22 in the form of charts, numerical values, and the like. In the present embodiment, the information provided by the external information-processing device 14 is viewable on the display 22 through a browser 23. The connection between the input unit 20 and the output unit 17 of the external information-processing device 14 may be provided in a wireless manner or the like, as well as in a wired manner.

The notification unit 24 is electrically connected to the control unit 21. When any abnormality in the patient or in any devices is detected during blood purification treatment, the notification unit 24 issues a predetermined notification (by, for example, outputting audio or a sound effect, turning on a warning lamp, making a warning lamp blink, or by any other like method) so as to let medical staffs therearound know the occurrence of the abnormality. The notification unit 24 according to the present embodiment is also capable of issuing the predetermined notification when any abnormality is found in the electrocardiogram acquired by the electrocardiogram-acquiring device 12, or when any blood leakage is detected by the blood-leakage-monitoring device 13.

The electrocardiogram-measuring devices 3 and 4 are closely attached to the skin of the patient and is capable of measuring the electrocardiogram (vital signs) of the patient. The electrocardiogram-measuring devices 3 and 4 include at least a pair of electrodes closely attached to respective positions that are across the heart from each other. The electrocardiogram-measuring devices 3 and 4 are electrically connected to the electrocardiogram-acquiring device 12. The electrocardiogram-acquiring device 12 acquires an electrocardiogram such as the one illustrated in FIG. 9 as an example (FIG. 9 illustrates a normal electrocardiogram) in real time on the basis of measurement signals transmitted from the electrocardiogram-measuring devices 3 and 4. The electrocardiogram normally has a waveform illustrated in FIG. 12. The wave height measured (the heights of the P wave, the R wave, the T wave, and the U wave) is calculated with reference to a baseline ($\beta$). In the normal electrocardiogram, as illustrated in FIG. 9, the baseline ($\beta$) is constant and stable.

The blood-leakage-detecting device 5 is attached to a position near the venous puncture needle (b) (the accessing unit) and is capable of detecting blood of the patient that may leak from the venous puncture needle (b). The blood-leakage-detecting device 5 is electrically connected to the blood-leakage-monitoring device 13. The blood-leakage-detecting device 5 according to the present embodiment includes predetermined electrode patterns (see FIG. 5). If any blood (blood or an infusion solution) leaks, a positive electrode pattern and a negative electrode pattern form a short circuit with the blood and then an electric current flows through the short circuit. Thus, blood leakage can be detected. The blood-leakage-detecting device 5 is electrically connected to the blood-leakage-monitoring device 13 that monitors whether or not any blood leakage has occurred on the basis of a detection signal transmitted from the blood-leakage-detecting device 5. The blood-leakage-monitoring device 13 is electrically connected to the input unit 20 of the blood purification device 1.

The medical apparatus according to the present embodiment includes the integrated detecting device 2 provided as a unit including the electrocardiogram-measuring device 4 and the blood-leakage-detecting device 5. As illustrated in FIGS. 4 to 6, the integrated detecting device 2 is a flexible sheet-like member having a close-contact surface 2a that is brought into close contact with the skin of the patient and a non-close-contact surface 2b that is out of close contact with the skin of the patient. The electrocardiogram-measuring device 4 is provided on the close-contact surface 2a. The blood-leakage-detecting device 5 is provided on the non-close-contact surface 2b. That is, the close-contact surface 2a and the non-close-contact surface 2b form the front surface and the back surface, respectively, of the integrated detecting device 2, one side (the front side) of which corresponds to the close-contact surface 2a and is provided with the electrocardiogram-measuring device 4, and the other side (the back side) of which corresponds to the non-close-contact surface 2b and is provided with the blood-leakage-detecting device 5.

To increase the closeness to the skin of the patient, gel is applied to an area of the close-contact surface 2a of the integrated detecting device 2 around the electrocardiogram-measuring device 4. Furthermore, an electrode D1 that is electrically connectable to the electrocardiogram-acquiring device 12 is provided at the proximal end part of the close-contact surface 2a of the integrated detecting device 2. The electrode D1 and the electrocardiogram-measuring device 4 are electrically connected to each other with a wiring line h provided in the form of a printed wiring pattern or a conductive wire. Hence, the measurement signal from the electrocardiogram-measuring device 4 is transmitted to the electrocardiogram-acquiring device 12. The non-close-contact surface 2b of the integrated detecting device 2 is provided at the proximal end part thereof with a pair of electrodes D2 (for example, a positive electrode and a negative electrode) that are electrically connectable to the blood-leakage-monitoring device 13. The electrodes D2 are electrically connected to the blood-leakage-detecting device 5. Hence, the detection signal from the blood-leakage-detecting device 5 is transmitted to the blood-leakage-monitoring device 13.

The integrated detecting device 2 further includes an insulating layer 2c (see FIG. 5) interposed between the close-contact surface 2a provided on the one side thereof and the non-close-contact surface 2b provided on the other side thereof, whereby the electrocardiogram-measuring device 4 and the blood-leakage-detecting device 5 are insulated from each other. Furthermore, adhesive is applied to the close-contact surface 2a of the integrated detecting device 2 so that the close-contact surface 2a adheres to the skin of the patient and allow the electrocardiogram-measuring device 4 to be in close contact with the patient. On the other hand, a moisture-absorbing member 2d (see FIG. 5) is attached to the non-close-contact surface 2b so that the blood that may leak from the venous puncture needle b (the accessing unit) can be absorbed (impregnated) and be detected by the blood-leakage-detecting device 5.

As illustrated in FIG. 4, the integrated detecting device 2 according to the present embodiment is held by a clip (H) and is attached to a position near the venous puncture needle b. As illustrated in FIGS. 7 and 8, the clip (H) includes an electrode E1 electrically connectable to the electrode D1 by being brought into contact therewith, a base portion H1 having the electrode E1 at the tip thereof, electrodes E2 electrically connectable to the pair of electrodes D2, respectively, by being brought into contact therewith, a pinching portion H2 having the electrodes E2 at the tip thereof, an attaching portion H3 fixable to the forceps-held flexible tube (g) (see FIG. 3) provided for the venous puncture needle (b), a leaf spring B constantly urging the pinching portion H2 in a direction away from the base portion H1, and a stopper S configured to bring the pinching portion H2 closer to the base portion H1 against the urging force exerted by the leaf spring B and to retain the pinching portion H2 at that close position.

With the electrode E1 facing the electrode D1 and the electrodes E2 facing the electrodes D2, the stopper S is operated such that the pinching portion H2 is brought closer to the base portion H1. Thus, as illustrated in FIGS. 5 and 7, the integrated detecting device 2 can be pinched with the electrode E1 being in contact with the electrode D1 and the electrodes E2 being in contact with the electrodes D2. Then, the attaching portion H3 is attached to the forceps-held flexible tube (g) with the venous puncture needle b stuck in the patient. Thus, the electrocardiogram-measuring device 4 is brought into close contact with the skin of the patient, and the blood-leakage-detecting device 5 is positioned near the venous puncture needle (b). When the stopper S is operated in the reverse direction, as illustrated in FIG. 8, the pinching portion H2 moves away from the base portion H1 with the urging force exerted by the leaf spring B. Therefore, the integrated detecting device 2 can be removed easily.

The electrocardiogram-acquiring device 12 is electrically connected to an input unit included in the external information-processing device 14. Hence, the electrocardiogram of the patient acquired in real time through the electrocardiogram-measuring devices 3 and 4 can be inputted into the input unit 15. The external information-processing device 14 is capable of receiving in real time and thus monitoring the electrocardiogram acquired by the electrocardiogram-acquiring device 12. As illustrated in FIG. 1, the external information-processing device 14 includes, in addition to the input unit 15, a checking unit 16, the output unit 17, a storing unit 18, and a display 19.

The checking unit 16 is electrically connected to the input unit 15 and is capable of checking whether or not the electrocardiogram received in real time by the input unit 15 meets predetermined conditions. In the present embodiment, the checking unit 16 is capable of checking whether or not the electrocardiogram received in real time contains any abnormality (for example, arrhythmia or the like recognized on the basis of the waveform of the electrocardiogram). Furthermore, the checking unit 16 according to the present embodiment is capable of detecting the coming off of the venous puncture needle (b) from the patient on the basis of the electrocardiogram received in real time.

Specifically, if the venous puncture needle (b) comes off the patient and the electrocardiogram-measuring device 4 is detached from the skin of the patient, the measured impedance changes. Consequently, as illustrated in a zone (a) in FIG. 10, the baseline of the electrocardiogram received in real time sharply changes. If such a sharp change in the baseline is detected, it is determined that the venous puncture needle b has come off (removed from) the patient. If perspiration of the patient causes the baseline to change, the baseline fluctuates gently as illustrated in FIG. 11. Hence, if such gentle fluctuation in the baseline is detected, it is determined that the fluctuation is caused by perspiration, not by the coming off of the venous puncture needle (b) from the patient.

Now, imagining various situations where the venous puncture needle (b) comes off the patient, methods of detecting such situations will be described.

(1) A Situation where Blood has Leaked from the Venous Puncture Needle b with the Integrated Detecting Device 2 being Correctly Held by the Clip H This situation corresponds to the following: a case where the arm of the patient into which the venous puncture needle (b) (an indwelling needle) has been shallowly stuck has moved and the tip of the needle has come off the blood vessel, a case where the fixing of the blood circuit (the arterial blood circuit 6a or the venous blood circuit 6b) at a position farther from the site where the venous puncture needle (b) is stuck has been loosened, or the like. Such a situation is accompanied by bleeding. Therefore, the blood adheres to the blood-leakage-detecting device 5 of the integrated detecting device 2 and lowers the resistance value between the electrodes. Hence, by detecting such a reduction in the resistance value, the above situation can be detected.

(2) A Situation where the Integrated Detecting Device 2 has Come Off the Clip H

This situation corresponds to the following: a case where the patient or the medical staff has unintentionally pulled the blood circuit, causing the venous puncture needle b to come off the patient; or the like. In such a situation, the integrated detecting device 2 and the clip H are detached from each other. Consequently, the outputs from both the electrocardiogram-acquiring device 12 and from the blood-leakage-monitoring device 13 stop. Hence, by detecting the stoppage of the outputs from the two, the above situation can be detected.

(3) A Situation where the Integrated Detecting Device 2 and the Venous Puncture Needle (b) Connected to Each Other with the Clip H have Come Off Altogether This situation corresponds to the following: a case where the patient or the medical staff has unintentionally pulled the blood circuit with the integrated detecting device 2 being loosely fixed to the skin of the patient, causing a unit of the integrated detecting device 2, the venous puncture needle b, and the clip H that are kept connected to one another to come off altogether; or the like. In such a situation, the electrocardiogram signal transmitted from the electrocardiogram-measuring device 4 is lost. Hence, by detecting the loss of the electrocardiogram signal, the above situation can be detected.

(4) A Situation where the Integrated Detecting Device 2 has Peeled Off the Skin of the Patient This situation corresponds to the following: a case where the integrated detecting device 2 peels off the skin of the patient because of factors such as perspiration, the dryness of the skin of the patient, or the thick body hair of the patient; or the like. In such a situation, the electrocardiogram signal transmitted from the electrocardiogram-measuring device 4 fluctuates or is lost. Hence, by detecting the fluctuation or the loss of the electrocardiogram signal, the above situation can be detected.

(5) A Situation where the Blood Circuit is Disconnected from the Venous Puncture Needle (b)

This situation corresponds to the following: a case where the locking of the joint c integrated with the venous puncture needle (b) by the lock ring L provided to the blood circuit is loose and the blood circuit is therefore disconnected from the venous puncture needle (b). In such a situation, if any blood adheres to the blood-leakage-detecting device 5, the resistance value between the electrodes is lowered. Hence, by detecting the reduction in the resistance value, the above situation can be detected. Even if no blood adheres to the blood-leakage-detecting device 5, the above situation may be detected if the electrocardiogram monitored through the electrocardiogram-acquiring device 12 indicates the occurrence of arrhythmia or the like.

The output unit 17 is electrically connected to the checking unit 16. If the checking unit 16 has determined that the predetermined conditions are met (in the present embodiment, if it is determined that the electrocardiogram received in real time contains any abnormality or that the venous puncture needle b has come off the patient), the output unit 17 can output the determination to the blood purification device 1. The storing unit 18 is electrically connected to the input unit 15 and is capable of memorizing and storing the electrocardiogram received in real time by the input unit 15 and other associated pieces of information (for example, waveform data and numerical values acquired since the start of the blood purification treatment, the occurrence history of abnormalities, data on past treatments, and so forth). The storing unit 18 is a memory included in the external information-processing device 14, a portable recording medium, or the like.

The display 19 is electrically connected to the input unit 15 and to the storing unit 18 and is capable of displaying the electrocardiogram received in real time by the input unit 15 and other associated pieces of information stored in the storing unit 18. The display 19 includes, for example, a liquid-crystal screen or the like. As described above, the blood purification device 1 according to the present embodiment includes the browser 23. The browser 23 is capable of issuing a request for the items displayed on the display 19 (for example, the browser 23 is capable of transmitting a request signal) and allows the items to be viewable on the display 22 in accordance with the request.

The input unit 20 of the blood purification device 1 according to the present embodiment is connected to the output unit 17 of the external information-processing device 14 and to the blood-leakage-monitoring device 13 and is capable of detecting the coming off of the venous puncture needle b (the accessing unit) from the patient on the basis of electrocardiographic information acquired through the output unit 17 from the electrocardiogram-acquiring device 12 and blood-leakage information acquired from the blood-leakage-monitoring device 13. If the coming off of the venous puncture needle b (the accessing unit) from the patient is detected, the notification unit 24 issues the predetermined notification.

The present embodiment employs the integrated detecting device 2 provided as a unit including the electrocardiogram-measuring device 4 closely attached to the skin of the patient and being capable of measuring the electrocardiogram of the patient, and the blood-leakage-detecting device 5 attached to a position near the venous puncture needle (b) (or the arterial puncture needle (a) and being capable of detecting blood of the patient that may leak from the venous puncture needle (b). Therefore, the measurement of the electrocardiogram and the detection of blood leakage occurring if the venous puncture needle b comes off the patient can be performed accurately without fail. Furthermore, the efficiency in the operation to be performed before and during the treatment (including the returning of the blood in the blood purification treatment) can be improved.

The integrated detecting device 2 according to the present embodiment has the close-contact surface 2a that is brought into close contact with the skin of the patient, and the non-close-contact surface 2b that is out of contact with the skin of the patient. The close-contact surface 2a is provided with the electrocardiogram-measuring device 4. The non-close-contact surface 2b is provided with the blood-leakage-detecting device 5. Hence, blood leakage that may occur if the venous puncture needle (b) comes off the patient can be detected assuredly while the electrocardiogram of the patient is measured accurately. In particular, the close-contact surface 2a and the non-close-contact surface 2b form the front surface and the back surface, respectively, of the integrated detecting device 2, one side of which corresponds to the close-contact surface 2a and is provided with the electrocardiogram-measuring device 4, and the other side of which corresponds to the non-close-contact surface 2b and is provided with the blood-leakage-detecting device 5. Hence, blood leakage that may occur if the venous puncture needle b comes off the patient can be detected more assuredly while the electrocardiogram of the patient is measured more accurately.

Furthermore, the integrated detecting device 2 according to the present embodiment is a flexible sheet-like member with the insulating layer 2c interposed between the close-contact surface 2a on one side thereof and the non-close-contact surface 2b on the other side thereof. Hence, the electrocardiogram-measuring device 4 provided on the flexible sheet-like member can be brought into close contact with the skin of the patient in a good manner, and the presence of the insulating layer 2c can prevent the occurrence of errors that may be caused by the interference between the measurement signal from the electrocardiogram-measuring device 4 and the detection signal from the blood-leakage-detecting device 5.

The close-contact surface 2a according to the present embodiment adheres to the skin of the patient and thus allows the electrocardiogram-measuring device 4 to be in close contact with the patient. Whereas, the non-close-contact surface 2b is provided with the moisture-absorbing member 2d, which absorbs blood that may leak from the venous puncture needle (b), whereby any blood leakage can be detected by the blood-leakage-detecting device 5. Hence, the detection of blood leakage by the blood-leakage-detecting device 5 can be performed more assuredly while the measurement of the electrocardiogram by the electrocardiogram-measuring device 4 is performed more accurately.

Furthermore, the electrocardiogram-acquiring device 12 acquires the electrocardiogram on the basis of the measurement signals transmitted from the electrocardiogram-measuring devices 3 and 4, and the blood-leakage-monitoring device 13 monitors whether or not there is any blood leakage on the basis of the detection signal transmitted from the blood-leakage-detecting device 5. Thus, the coming off of the venous puncture needle b from the patient can be detected on the basis of the electrocardiographic information acquired by the electrocardiogram-acquiring device 12 and the blood-leakage information acquired by the blood-leakage-monitoring device 13. Hence, the occurrence of any blood leakage from the venous puncture needle b can be detected not only by the blood-leakage-monitoring device 13 but also by the electrocardiogram-acquiring device 12.

While an embodiment of the present invention has been described above, the present invention is not limited thereto. For example, applicable treatment devices include not only the blood purification device 1 but also an infusion device including an accessing unit formed of a catheter that is insertable into a blood vessel of a patient. Moreover, the integrated detecting device 2 provided as a unit including the electrocardiogram-measuring device 4 and the blood-leakage-detecting device 5 is not limited to a flexible sheet-like member and may be a block-like member or the like. For example, the electrocardiogram-measuring device 4 may be provided on the front side (the close-contact surface that is brought into contact with the skin) of a wing part of a winged needle, and the blood-leakage-detecting device 5 may be provided on the back side (the non-close-contact surface that is out of contact with the skin) of the wing part.

While the integrated detecting device 2 according to the above embodiment is attached to a position near the venous puncture needle (b), the integrated detecting device 2 may be attached to another position near the other accessing unit such as the arterial puncture needle a or may be fixed to a position near the accessing unit by using any member other than the clip H. Furthermore, the integrated detecting device 2 may include a plurality of (two or more) electrocardiogram-measuring electrodes 4 so that measured values acquired by the plurality of electrocardiogram-measuring electrodes 4 can be compared with one another. Thus, for example, a situation where the fixing of the venous puncture needle (b) (or the arterial puncture needle (a) is loose (such as a situation where the adhesive tape almost peels off) may be detected. In addition, the function of the external information-processing device 14 may be imparted to the blood purification device 1, whereby an abnormal signal generated by the external information-processing device 14 may be inputted ultimately to the blood purification device 1 via a central monitoring device.

The present invention is applicable to any medical apparatus having a different external shape, additional functions, or the like, as long as the apparatus includes an integrated detecting device provided as a unit including an electrocardiogram-measuring device and a blood-leakage-detecting device.

REFERENCE SIGNS 1 blood purification device
2 integrated detecting device
2a close-contact surface
2b non-close-contact surface
3 electrocardiogram-measuring device
4 electrocardiogram-measuring device
5 blood-leakage-detecting device
6a arterial blood circuit
6b venous blood circuit
7 dialyzer (blood purifier)
8 blood pump
9a arterial air-trap chamber
9b venous air-trap chamber
10 duplex pump
11 ultrafiltration pump
12 electrocardiogram-acquiring device
13 blood-leakage-monitoring device
14 external information-processing device
15 input unit
16 checking unit
17 output unit
18 storing unit
19 display
20 input unit
21 control unit
22 display
23 browser
24 notification unit

The invention claimed is:

1. A medical apparatus comprising:
a treatment device including an accessing unit formed of either a puncture needle stickable into a patient or a catheter insertable into a blood vessel of the patient;
an electrocardiogram-measuring device configured to be closely attached to a skin of the patient and being capable of measuring an electrocardiogram of the patient; and
a blood-leakage-detecting device attached to a position near the accessing unit and being capable of detecting blood of the patient that may leak from the accessing unit,
an integrated detecting device provided as a unit, which includes the electrocardiogram-measuring device and the blood-leakage-detecting device;
wherein the integrated detecting device has a close-contact surface that is brought into close contact with the skin of the patient and a non-close-contact surface that is out of close contact with the skin of the patient, the close-contact surface being provided with the electrocardiogram-measuring device and an electrode that is electrically connectable to the electrocardiogram-measuring device and the non-close-contact surface being provided with the blood-leakage-detecting device and an electrode that is electrically connectable to the blood-leakage-detecting device; and
wherein the integrated detecting device is a flexible sheet-like member with an insulating layer interposed between the close-contact surface on one side and the non-close-contact surface on an other side thereof so that the electrocardiogram-measuring device and the blood-leakage-detecting device are electrically insulated from each other;
wherein the medical apparatus includes a clip that attaches the integrated detecting device at a position near the puncture needle; and
wherein the clip includes a stopper that moves two opposing pinching portions towards each other.

2. The medical apparatus according to claim 1, wherein the close-contact surface and the non-close-contact surface are a front surface and a back surface, respectively, of the integrated detecting device, one side of which corresponds to the close-contact surface and is provided with the electrocardiogram-measuring device, and an other side of which corresponds to the non-close-contact surface and is provided with the blood-leakage-detecting device.

3. The medical apparatus according to claim 2, wherein the close-contact surface adheres to the skin of the patient and allows the electrocardiogram-measuring device to be in close contact with the patient, and the non-close-contact surface is provided with a moisture-absorbing member, the moisture-absorbing member absorbing blood that may leak from the accessing unit and allowing the blood-leakage-detecting device to detect blood leakage.

4. The medical apparatus according to claim 3, further comprising:
an electrocardiogram-acquiring device that acquires the electrocardiogram on the basis of a measurement signal transmitted from the electrocardiogram-measuring device; and
a blood-leakage-monitoring device that monitors whether or not there is any blood leakage on the basis of a detection signal transmitted from the blood-leakage-detecting device,
wherein coming off of the accessing unit from the patient is detectable on the basis of electrocardiographic information acquired by the electrocardiogram-acquiring device and blood-leakage information acquired by the blood-leakage-monitoring device.

5. The medical apparatus according to claim 2, further comprising:
an electrocardiogram-acquiring device that acquires the electrocardiogram on the basis of a measurement signal transmitted from the electrocardiogram-measuring device; and
a blood-leakage-monitoring device that monitors whether or not there is any blood leakage on the basis of a detection signal transmitted from the blood-leakage-detecting device,
wherein coming off of the accessing unit from the patient is detectable on the basis of electrocardiographic information acquired by the electrocardiogram-acquiring device and blood-leakage information acquired by the blood-leakage-monitoring device.

6. The medical apparatus according to claim 1, further comprising:
an electrocardiogram-acquiring device that acquires the electrocardiogram on the basis of a measurement signal transmitted from the electrocardiogram-measuring device; and
a blood-leakage-monitoring device that monitors whether or not there is any blood leakage on the basis of a detection signal transmitted from the blood-leakage-detecting device,
wherein coming off of the accessing unit from the patient is detectable on the basis of electrocardiographic information acquired by the electrocardiogram-acquiring device and blood-leakage information acquired by the blood-leakage-monitoring device.

7. The medical apparatus according to claim 1, wherein the blood-leakage-detecting device includes a pair of electrodes that are in communication with a blood-leakage monitoring device.

8. The medical apparatus according to claim 7, wherein the pair of electrodes are a positive electrode and a negative electrode.

9. The medical apparatus according to claim 1, wherein the clip includes an attaching portion that 9 connects the clip to the puncture needle.

10. The medical apparatus of claim 1, wherein the electrocardiogram-measuring device includes a checking unit that is electrically connected to an input unit that checks whether the electrocardiogram received in real time by the input meets predetermined conditions.

11. The medical apparatus according to claim 1, wherein the clip includes a leaf spring that urges the pinching portions away from each other.

12. A medical apparatus comprising:
a treatment device including an accessing unit formed of either a puncture needle stickable into a patient or a catheter insertable into a blood vessel of the patient;
an electrocardiogram-measuring device configured to be closely attached to a skin of the patient and being capable of measuring an electrocardiogram of the patient; and
a blood-leakage-detecting device attached to a position near the accessing unit and being capable of detecting blood of the patient that may leak from the accessing unit,
an integrated detecting device provided as a unit, which includes the electrocardiogram-measuring device and the blood-leakage-detecting device;
wherein the integrated detecting device has a close-contact surface that is brought into close contact with the skin of the patient and a non-close-contact surface that is out of close contact with the skin of the patient, the close-contact surface being provided with the electrocardiogram-measuring device and an electrode that is electrically connectable to the electrocardiogram-measuring device and the non-close-contact surface being provided with the blood-leakage-detecting device and an electrode that is electrically connectable to the blood-leakage-detecting device;
wherein the medical apparatus includes a clip that attaches the integrated detecting device at a position near the puncture needle; and
wherein the clip includes a first electrode and a second electrode that are moved toward each other to a first electrode and a second electrode of the integrated detecting device to both electrically connect the clip and the integrated detecting device and to attach the integrated detecting device in a position near the puncture needle.

13. The medical apparatus of claim 12, wherein the electrocardiogram-measuring device and the blood-leakage-detecting device are separated by an insulating layer that electrically insulates the electrocardiogram-measuring device and the blood-leakage-detecting device from each other.

14. The medical apparatus according to claim 12, wherein the clip includes a first pinching portion and a second pinching portion that are movable relative to each other to pinch the integrated detecting device therebetween.

15. The medical apparatus according to claim 12, wherein the clip includes a stopper that moves two opposing pinching portions towards each other.

16. A medical apparatus comprising:
a treatment device including an accessing unit formed of either a puncture needle stickable into a patient or a catheter insertable into a blood vessel of the patient
an electrocardiogram-measuring device configured to be closely attached to a skin of the patient and being capable of measuring an electrocardiogram of the patient and
a blood-leakage-detecting device attached to a position near the accessing unit and being capable of detecting blood of the patient that may leak from the accessing unit,
an integrated detecting device provided as a unit, which includes the electrocardiogram-measuring device and the blood-leakage-detecting device;
wherein the integrated detecting device has a close-contact surface that is brought into close contact with the skin of the patient and a non-close-contact surface that is out of close contact with the skin of the patient, the close-contact surface being provided with the electrocardiogram-measuring device and an electrode that is electrically connectable to the electrocardiogram-measuring device and the non-close-contact surface being provided with the blood-leakage-detecting device and an electrode that is electrically connectable to the blood-leakage-detecting device; and
wherein the integrated detecting device is a flexible sheet-like member with an insulating layer interposed between the close-contact surface on one side and the non-close-contact surface on an other side thereof so that the electrocardiogram-measuring device and the blood-leakage-detecting device are electrically insulated from each other;

wherein the medical apparatus includes a clip that attaches the integrated detecting device at a position near the puncture needle; and wherein the clip includes a first pinching portion and a second pinching portion that are movable relative to each other to pinch the integrated detecting device therebetween.

17. The medical apparatus according to claim 16, wherein the clip includes a stopper that moves two opposing pinching portions towards each other.

18. The medical apparatus of claim 16, wherein the electrocardiogram-measuring device includes a checking unit that is electrically connected to an input unit that checks whether the electrocardiogram received in real time by the input meets predetermined conditions.

19. The medical apparatus according to claim 16, wherein the clip includes an attaching portion that connects the clip to the puncture needle.

20. The medical apparatus according to claim 16, wherein the close-contact surface and the non-close-contact surface are a front surface and a back surface, respectively, of the integrated detecting device, one side of which corresponds to the close-contact surface and is provided with the electrocardiogram-measuring device, and an other side of which corresponds to the non-close-contact surface and is provided with the blood-leakage-detecting device.

* * * * *